(12) United States Patent
Edic et al.

(10) Patent No.: US 7,852,979 B2
(45) Date of Patent: Dec. 14, 2010

(54) DUAL-FOCUS X-RAY TUBE FOR RESOLUTION ENHANCEMENT AND ENERGY SENSITIVE CT

(75) Inventors: Peter Michael Edic, Albany, NY (US); Samit Kumar Basu, Fremont, CA (US)

(73) Assignee: General Electric Company, Niskayuna, NY (US)

( * ) Notice: Subject to any disclaimer, the term of this patent is extended or adjusted under 35 U.S.C. 154(b) by 93 days.

(21) Appl. No.: 11/954,295

(22) Filed: Dec. 12, 2007

(65) Prior Publication Data
US 2008/0247504 A1  Oct. 9, 2008

Related U.S. Application Data

(60) Provisional application No. 60/910,265, filed on Apr. 5, 2007.

(51) Int. Cl.
| | |
|---|---|
| A61B 6/03 | (2006.01) |
| H05G 1/60 | (2006.01) |
| H05G 1/64 | (2006.01) |
| H01J 35/06 | (2006.01) |
| H01J 35/30 | (2006.01) |

(52) U.S. Cl. ............... 378/16; 378/5; 378/98.9; 378/134; 378/137

(58) Field of Classification Search ............ 378/5, 378/16, 98.9, 98.11, 124, 125, 134, 137, 378/138
See application file for complete search history.

(56) References Cited

U.S. PATENT DOCUMENTS

| | | | | |
|---|---|---|---|---|
| 6,256,369 | B1 * | 7/2001 | Lai | 378/14 |
| 6,480,572 | B2 * | 11/2002 | Harris et al. | 378/136 |
| 6,560,315 | B1 * | 5/2003 | Price et al. | 378/144 |
| 6,650,730 | B2 * | 11/2003 | Bogatu et al. | 378/158 |
| 6,735,273 | B2 * | 5/2004 | Flohr et al. | 378/5 |
| 6,882,703 | B2 * | 4/2005 | Price et al. | 378/91 |
| 6,901,131 | B2 | 5/2005 | Edic et al. | |

(Continued)

OTHER PUBLICATIONS

Robert E. Alvarez et al. Energy-selective Reconstruction in X-ray Computerized Tomography; Phys. Med. Biol., 1976, 733-744; vol. 21, No. 5.

*Primary Examiner*—Allen C. Ho
(74) *Attorney, Agent, or Firm*—Joseph J. Christian

(57) ABSTRACT

A CT system includes a rotatable gantry having an opening for receiving an object to be scanned, at least one x-ray source coupled to the gantry and configured to project x-rays toward the object, a detector coupled to the gantry and having a scintillator therein and configured to receive x-rays that pass through the object, and a generator configured to energize the at least one x-ray source. The system includes a controller configured to energize the generator to project a first beam of x-rays toward the object from a first focal spot position of an anode, the first beam of x-rays having a ray traversing a path through the object, acquire imaging data from the first beam of x-rays, position the at least one x-ray source such that a second beam of x-rays projected from a second focal spot position of the anode has a ray directed to traverse the path through the object, the second anode focal spot position different than the first anode focal spot position, energize the generator to project the second beam of x-rays toward the object, and acquire imaging data from the second beam of x-rays.

20 Claims, 8 Drawing Sheets

U.S. PATENT DOCUMENTS

| | | | |
|---|---|---|---|
| 6,904,118 B2 | 6/2005 | Wu et al. | |
| 6,947,522 B2 * | 9/2005 | Wilson et al. | 378/125 |
| 6,968,039 B2 * | 11/2005 | Lemaitre et al. | 378/138 |
| 6,975,703 B2 * | 12/2005 | Wilson et al. | 378/124 |
| 6,980,623 B2 * | 12/2005 | Dunham et al. | 378/19 |
| 6,983,035 B2 * | 1/2006 | Price et al. | 378/124 |
| 7,003,077 B2 * | 2/2006 | Jen et al. | 378/124 |
| 7,065,179 B2 * | 6/2006 | Block et al. | 378/134 |
| 7,082,182 B2 | 7/2006 | Zhou et al. | |
| 7,120,222 B2 * | 10/2006 | Hoffman | 378/5 |
| 7,187,756 B2 * | 3/2007 | Gohno et al. | 378/124 |
| 7,203,268 B2 * | 4/2007 | Yahata | 378/4 |
| 7,203,274 B2 * | 4/2007 | Charles et al. | 378/54 |
| 7,206,373 B2 * | 4/2007 | Seufert | 378/9 |
| 7,305,063 B2 * | 12/2007 | Heuscher | 378/12 |
| 7,366,280 B2 * | 4/2008 | Lounsberry | 378/12 |
| 7,426,260 B2 * | 9/2008 | Cantu et al. | 378/98.8 |
| 7,496,180 B1 * | 2/2009 | Subraya et al. | 378/137 |
| 7,529,344 B2 * | 5/2009 | Oreper | 378/134 |
| 7,746,974 B2 * | 6/2010 | Shukla | 378/4 |
| 7,778,383 B2 * | 8/2010 | Koehler et al. | 378/5 |
| 2004/0247082 A1 * | 12/2004 | Hoffman | 378/119 |
| 2005/0084060 A1 * | 4/2005 | Seppi et al. | 378/5 |

* cited by examiner

DUAL-FOCUS X-RAY TUBE FOR RESOLUTION ENHANCEMENT AND ENERGY SENSITIVE CT

CROSS REFERENCE TO RELATED APPLICATION

The present application claims the benefit of U.S. Provisional Application Ser. No. 60/910,265, filed Apr. 5, 2007.

BACKGROUND OF THE INVENTION

The present invention relates generally to diagnostic imaging and, more particularly, to an apparatus and method of acquiring imaging data at more than one energy range using a multi-energy imaging source modulated at multiple-view intervals.

Typically, in computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT imaging system may include an energy sensitive (ES), multi-energy (ME), and/or dual-energy (DE) CT imaging system that may be referred to as an ESCT, MECT, and/or DECT imaging system, in order to acquire data for material decomposition or effective Z estimation. Such systems may use a scintillator or a direct conversion detector material in lieu of the scintillator. The ESCT, MECT, and/or DECT imaging system in an example is configured to be responsive to different x-ray spectra. For example, a conventional third-generation CT system may acquire projections sequentially at different peak kilovoltage (kVp) operating levels of the x-ray tube, which changes the peak and spectrum of energy of the incident photons comprising the emitted x-ray beams. Energy sensitive detectors may be used such that each x-ray photon reaching the detector is recorded with its photon energy.

Techniques to obtain energy sensitive measurements comprise: (1) scan with two distinctive energy spectra, and (2) detect photon energy according to energy deposition in the detector. ESCT/MECT/DECT provides energy discrimination and material characterization. For example, in the absence of object scatter, the system derives the behavior at a different energy based on the signal from two relative regions of photon energy from the spectrum: the low-energy and the high-energy portions of the incident x-ray spectrum. In a given energy region relevant to medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials, or the effective atomic number distribution with the scanned object.

A principle objective of energy sensitive scanning is to obtain diagnostic CT images that enhance information (contrast separation, material specificity, etc.) within the image by utilizing two scans at different chromatic energy states. A number of techniques have been proposed to achieve energy sensitive scanning including acquiring two scans either (1) back-to-back sequentially in time where the scans require two rotations of the gantry around the subject, or (2) interleaved as a function of the rotation angle requiring one rotation around the subject, in which the tube operates at, for instance, 80 kVp and 140 kVp potentials. High frequency generators have made it possible to switch the kVp potential of the high frequency electromagnetic energy projection source on alternating views. As a result, data for two energy sensitive scans may be obtained in a temporally interleaved fashion rather than two separate scans made several seconds apart as required with previous CT technology.

However, taking separate scans several seconds apart from one another may result in mis-registration between datasets caused by patient motion (both external patient motion and internal organ motion) and different cone angles. And, in general, a conventional two-pass dual kVp technique cannot be applied reliably where small details need to be resolved for body features that are in motion.

Another technique to acquire projection data for material decomposition includes using energy sensitive detectors, such as a CZT or other direct conversion material having electronically pixelated structures or anodes attached thereto. However, this technology typically has a low saturation flux rate that may be insufficient, and the maximum photon-counting rate achieved by the current technology may be two or more orders of magnitude below what is necessary for general-purpose medical CT applications.

Therefore, it would be desirable to design an apparatus and method of acquiring imaging data at more than one energy range using an imaging source modulated at multiple-view intervals and positioned to generate overlapping views of imaging data having energy discriminating capability.

BRIEF DESCRIPTION OF THE INVENTION

Embodiments of the invention are directed to a method and apparatus for acquiring imaging data at more than one energy range that overcome the aforementioned drawbacks.

An energy discriminating CT detector is disclosed. Embodiments of the invention support the acquisition of both anatomical detail as well as tissue characterization information for medical CT, and for components within luggage. Energy discriminatory information or data may be used to reduce the effects of beam hardening and the like. The detector supports the acquisition of tissue discriminatory data and therefore provides diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization. For baggage scanning, the effective atomic number generated from energy sensitive CT principles allows reduction in image artifacts, such as beam hardening, as well as provides addition discriminatory information for false alarm reduction.

According to an aspect of the invention, a CT system includes a rotatable gantry having an opening for receiving an object to be scanned, at least one x-ray source coupled to the gantry and configured to project x-rays toward the object, a detector coupled to the gantry and having a scintillator therein and configured to receive x-rays that pass through the object, and a generator configured to energize the at least one x-ray source. The system includes a controller configured to energize the generator to project a first beam of x-rays toward the object from a first focal spot position of an anode, the first beam of x-rays having a ray traversing a path through the object, acquire imaging data from the first beam of x-rays, position the at least one x-ray source such that a second beam of x-rays projected from a second focal spot position of the anode has a ray directed to traverse the path through the object, the second anode focal spot position different than the first anode focal spot position, energize the generator to project the second beam of x-rays toward the object, and acquire imaging data from the second beam of x-rays.

According to another aspect of the invention, a method of acquiring energy sensitive CT imaging data includes moving a first focal spot of an x-ray source to a first position with respect to an object to be scanned, projecting a first beam of x-ray energy toward an object from the first focal spot positioned in the first position, and acquiring a first projection of imaging data from the first beam of x-ray energy. The method further includes projecting a second beam of x-ray energy toward the object from a second focal spot positioned in the first position, the second focal spot being positioned at a different position on an anode than the first focal spot and acquiring a second projection of imaging data from the second beam of x-ray energy.

According to yet another aspect of the invention, a controller is configured to acquire imaging data, the controller having instructions to project at least one beam of x-rays through an object to be imaged, acquire a first set of projection data of the object from a source positioned at a first location, and acquire a second set of projection data of the object from a source positioned at a second location different from the first location, wherein the second set of projection data is oriented, within the object, with the first set of projection data.

These and other advantages and features will be more readily understood from the following detailed description of preferred embodiments of the invention that is provided in connection with the accompanying drawings.

DETAILED DESCRIPTION OF THE PREFERRED EMBODIMENT

Diagnostics devices comprise x-ray systems, magnetic resonance (MR) systems, ultrasound systems, computed tomography (CT) systems, positron emission tomography (PET) systems, nuclear medicine, and other types of imaging systems. Applications of x-ray sources comprise imaging, medical, security, and industrial inspection applications. However, it will be appreciated by those skilled in the art that an implementation is applicable for use with single-slice, other multi-slice, or volumetric configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of embodiments of the invention is described with respect to a sixty-four-slice computed tomography (CT) system. However, it will be appreciated by those skilled in the art that embodiments of the invention are equally applicable for use with other multi-slice or volumetric configurations.

Figure 1:
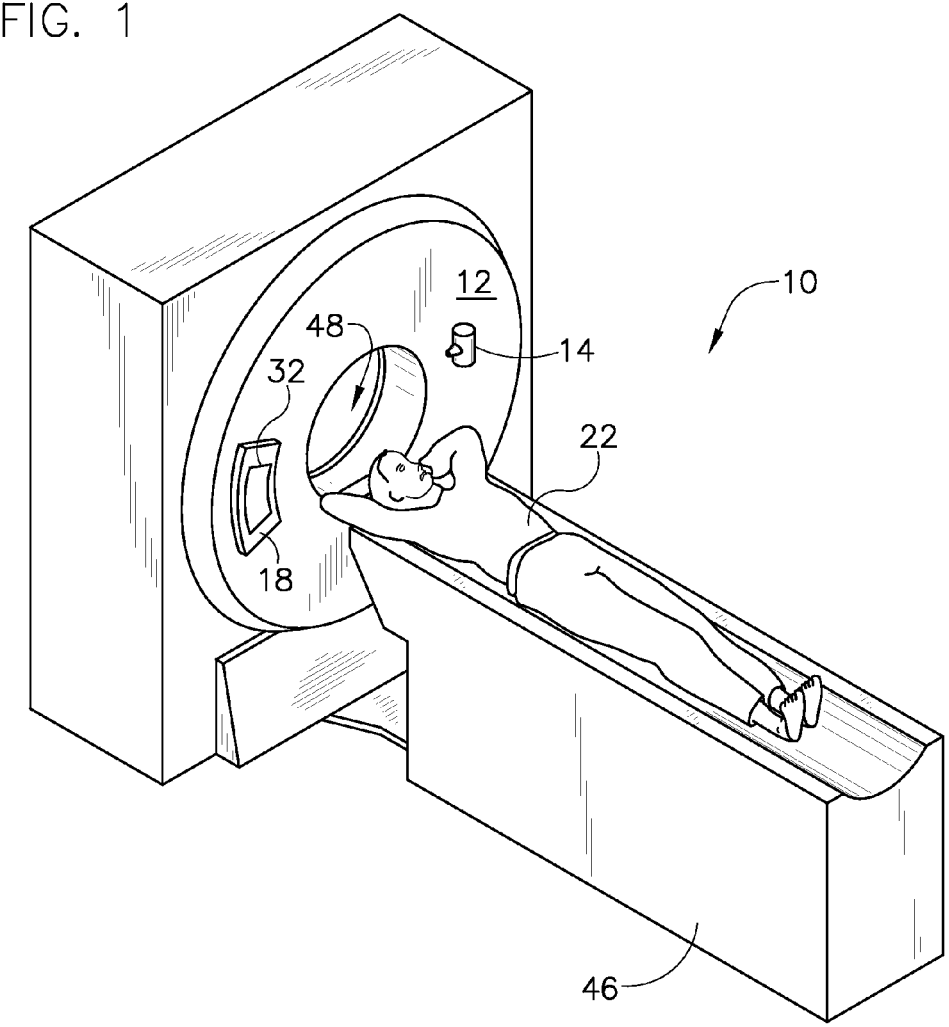
FIG. 1 is a pictorial view of a CT imaging system.
Figure 2:
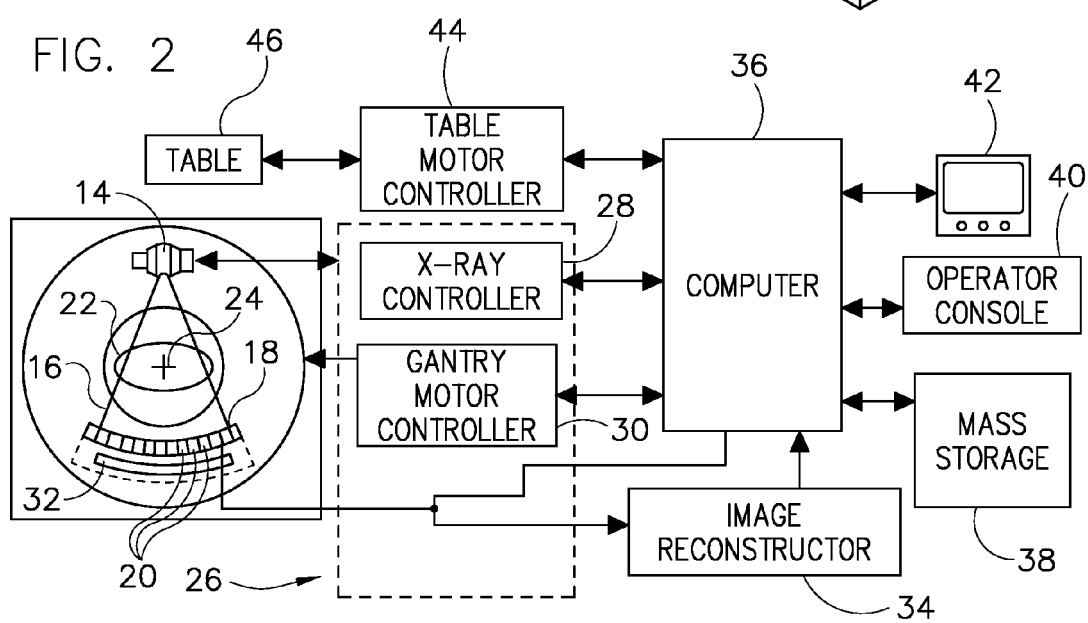
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a polychromatic beam of x-rays 16 (FIG. 2) toward a detector assembly 18 or collimator 19 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a subject 22, here shown as a medical patient, and DAS 32 converts the data to digital signals for subsequent processing. Each detector 20 produces an analog electrical signal that represents the intensity of an impinging x-ray beam and hence the attenuated beam as it passes through the subject 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high-speed reconstruction. The reconstructed image is applied as an input to a computer 36, which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator-supplied commands and parameters are used by computer 36 to provide control signals and information to DAS 32, x-ray controller 28 and gantry motor controller 30. In addition, computer 36 operates a table motor controller 44, which controls a motorized table 46 to position subject 22 and gantry 12. Particularly, table 46 moves subjects 22 through a gantry opening 48 of FIG. 1 in whole or in part.

Figure 3:
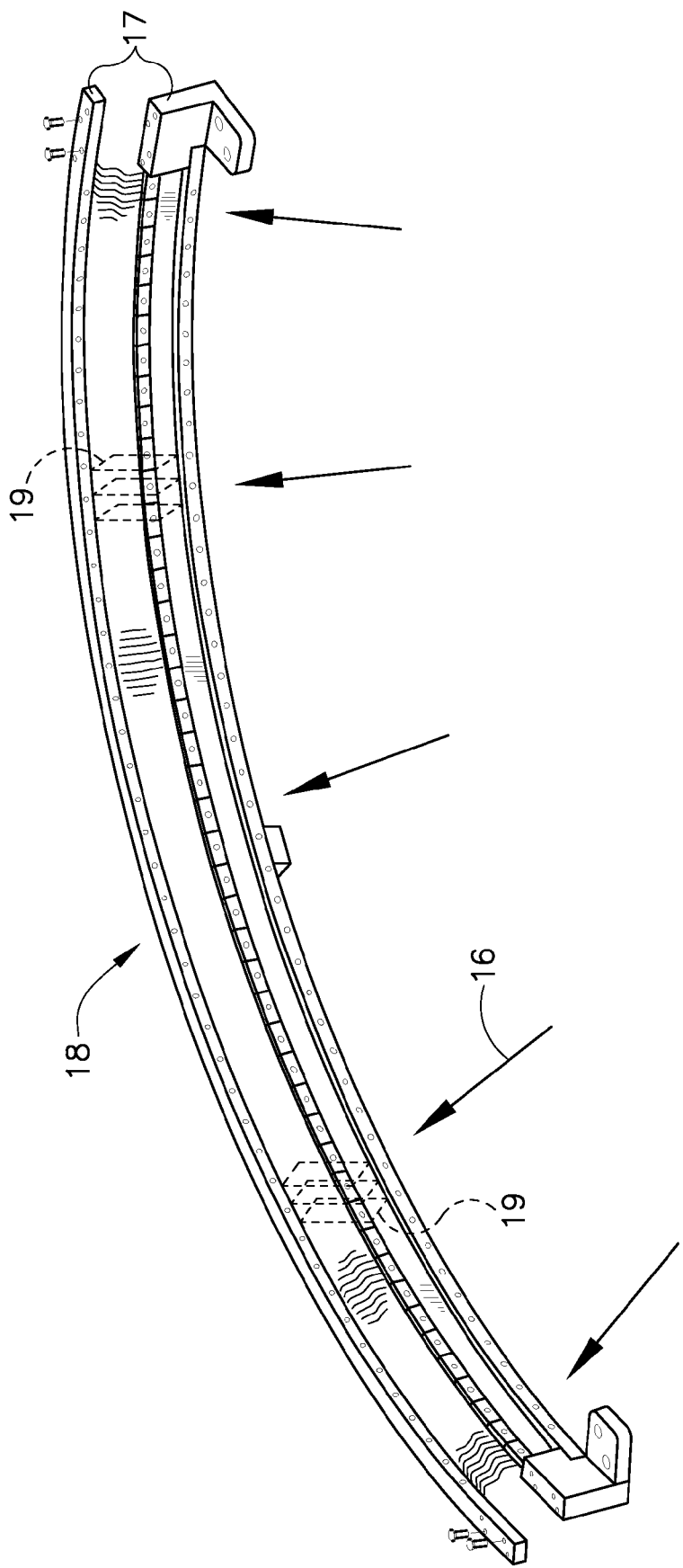
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
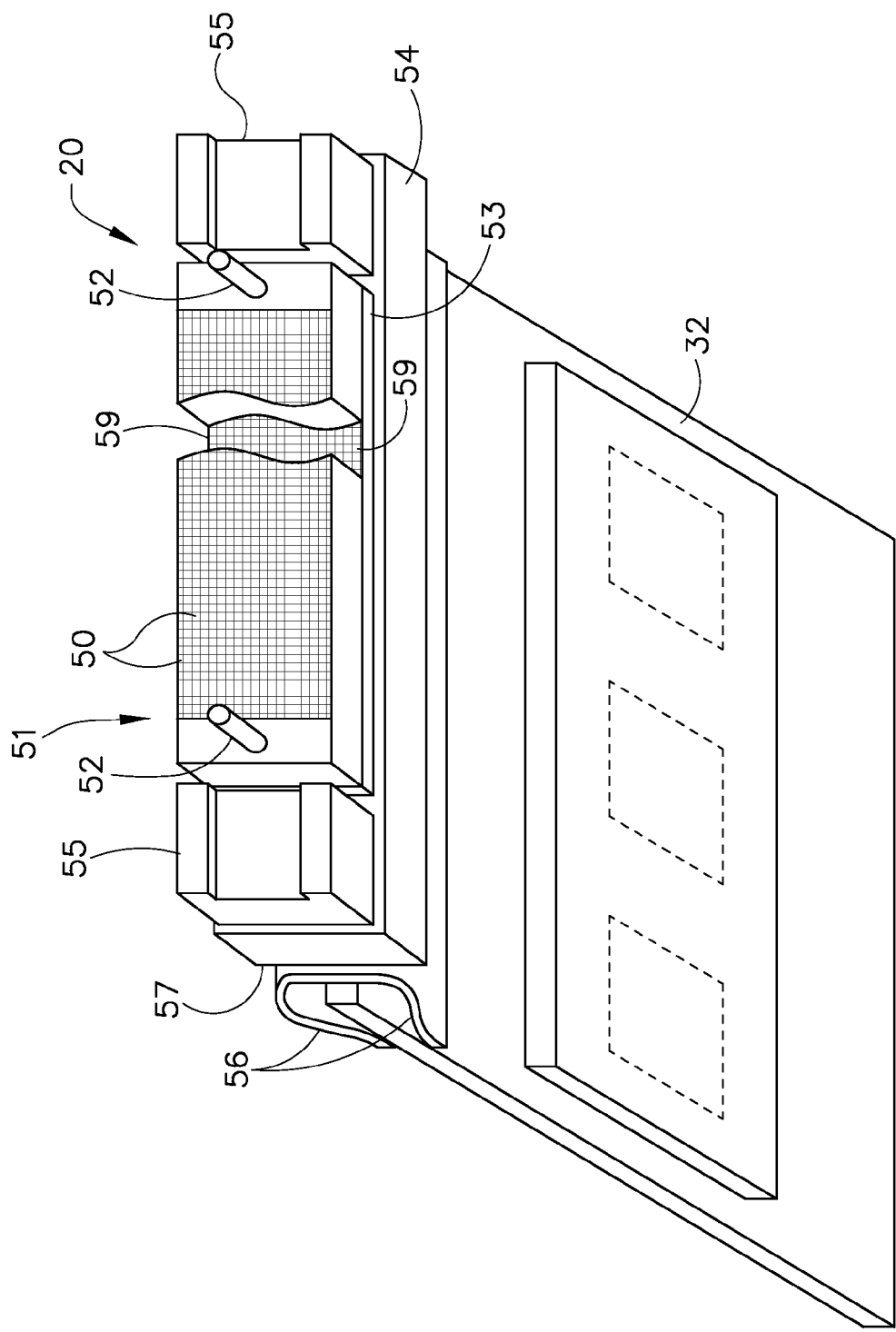
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within the backlit diode array 53. The analog signal generated is carried through the multi-layer substrate 54, through the flex circuits 56, to DAS 32 wherein the analog signal is converted to a digital signal.

Figure 5:
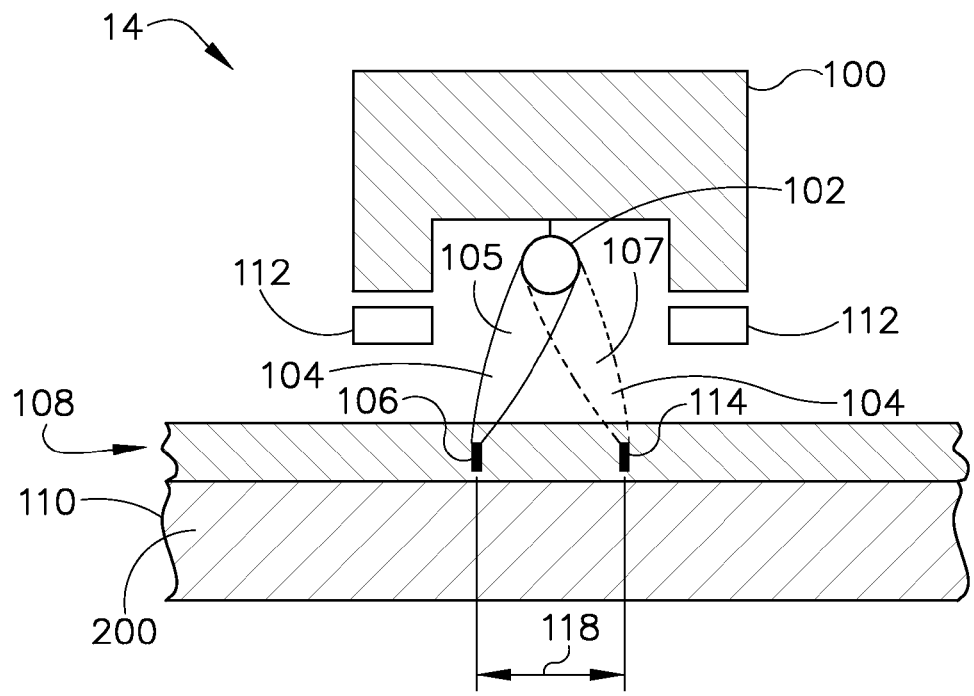
FIG. 5 is a schematic view of an x-ray tube having a cathode with one filament according to embodiments of the invention.

Referring now to FIG. 5, x-ray source 14 is shown according to an embodiment of the invention as including a cathode 100 having a single filament 102. A beam of electrons 104 is emitted from the filament 102 to a first focal spot 106 on an anode 200 of x-ray source 14. The anode 200 includes a beveled surface 108 positioned on a base 110 of the anode 200. The beam of electrons 104 is electromagnetically or electrostatically deflected by the use of a pair of electrodes 112 having the beam of electrons 104 passing therethrough. By applying an electromagnetic or electrostatic field to the electrodes 112, the beam of electrons 104 emit along path 105 to the position of first focal spot 106. The beam of electrons 104 may likewise be directed along a second path 107 to the position of a second focal spot 114 on anode 200 by appropriately altering the electromagnetic or electrostatic field. Accordingly, the beam of electrons 104 emitted from a single filament 102 may be rapidly wobbled to impinge upon the anode 200 at focal spots 106, 114, by altering the field applied to the electrodes 112.

Figure 6:
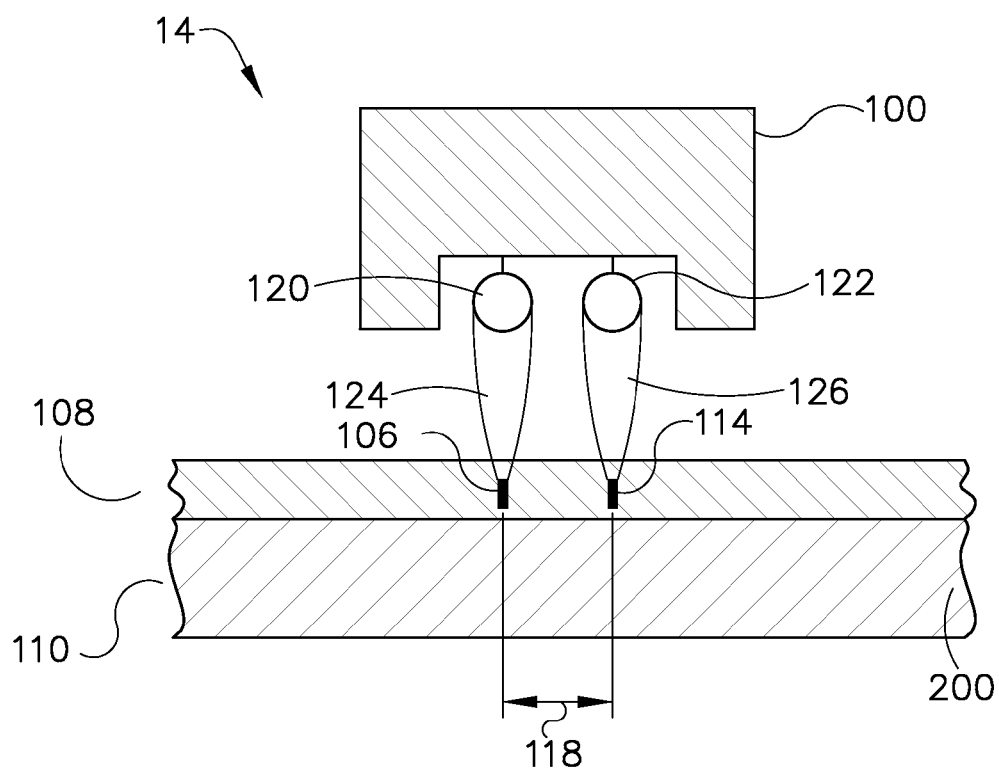
FIG. 6 is a schematic view of an x-ray tube having a cathode with two filaments according to embodiments of the invention.

Referring now to FIG. 6, x-ray source 14 is shown according to another embodiment of the invention wherein the cathode 100 has two filaments 120, 122, positioned therein. In this embodiment, electrons may be directed from a first filament 120 to the anode 200 along a path 124, which impinge thereon at the first focal spot 106. Likewise, electrons may be directed from the second filament 122 along a path 126 to the anode 200, which impinge thereon at the second focal spot 114. Accordingly, FIG. 6 illustrates a cathode 100 having two filaments 120, 122 that direct electrons to the two focal spots 106, 114 without the need for electrostatic or electromagnetic deflection as illustrated in FIG. 5.

Referring to both FIGS. 5 and 6, in one embodiment of the invention, electrons directed toward the two focal spots 106, 114, may be at substantially the same kVp. Specifically, referring to FIG. 5, electrons may be caused to emit from the filament 102 to the first focal spot 106 at a first kVp such as 140 kVp, and electrons may next be caused to emit from the filament 102 to the second focal spot 114, also at substantially the same kVp, after the beam of electrons 104 is wobbled from the first path 105 to the second path 107. Likewise, referring to FIG. 6, electrons may be caused to emit from the first filament 120 and along the path 124 to the first focal spot 106 at a first kVp, and electrons may be caused to emit from the second filament 122 and along the path 126 to the second focal spot 114, also at substantially the first kVp. In this manner, x-rays emitting from focal spot 106 and x-rays emitting from focal spot 114 have substantially the same energy.

Referring again to both FIGS. 5 and 6, in another embodiment of the present invention, electron emission toward the two focal spots 106, 114, may be at different kVps. Specifically, referring to FIG. 5, electrons may be caused to emit from the filament 102 to the first focal spot 106 at a first kVp, and electrons may next be caused to emit from the filament 102 to the second focal spot 114 at a second kVp, after the beam of electrons 104 is wobbled from along the first path 105 to along the second path 107. Likewise, referring to FIG. 6, electrons may be caused to emit from the first filament 120 and along the path 124 to the first focal spot 106 at a first kVp, and electrons may be caused to emit from the second filament 122 and along the path 126 to the second focal spot 114, at the second kVp. In this manner, x-rays emitting from focal spot 106 and x-rays emitting from focal spot 114 have different energies.

In addition to the energy sensitive capability of the embodiment described herein, one skilled in the art will recognize that because of the relatively close spacing 118 between the first focal spot 106 and the second focal spot 114, resolution of the imaging system 10 may be enhanced over conventional single-focal spot CT systems. In other words, for the embodiments described herein, whether the x-rays emit from the focal spots 106, 114 by wobbling as described with respect to FIG. 5, or by discretely positioning two separate filaments 120, 122 as described with respect to FIG. 6, such close spacing between the two focal spots 106, 114 causes resolution of the system to be improved over a conventional CT system having typically a single focal spot emission during a scan.

Figure 7:
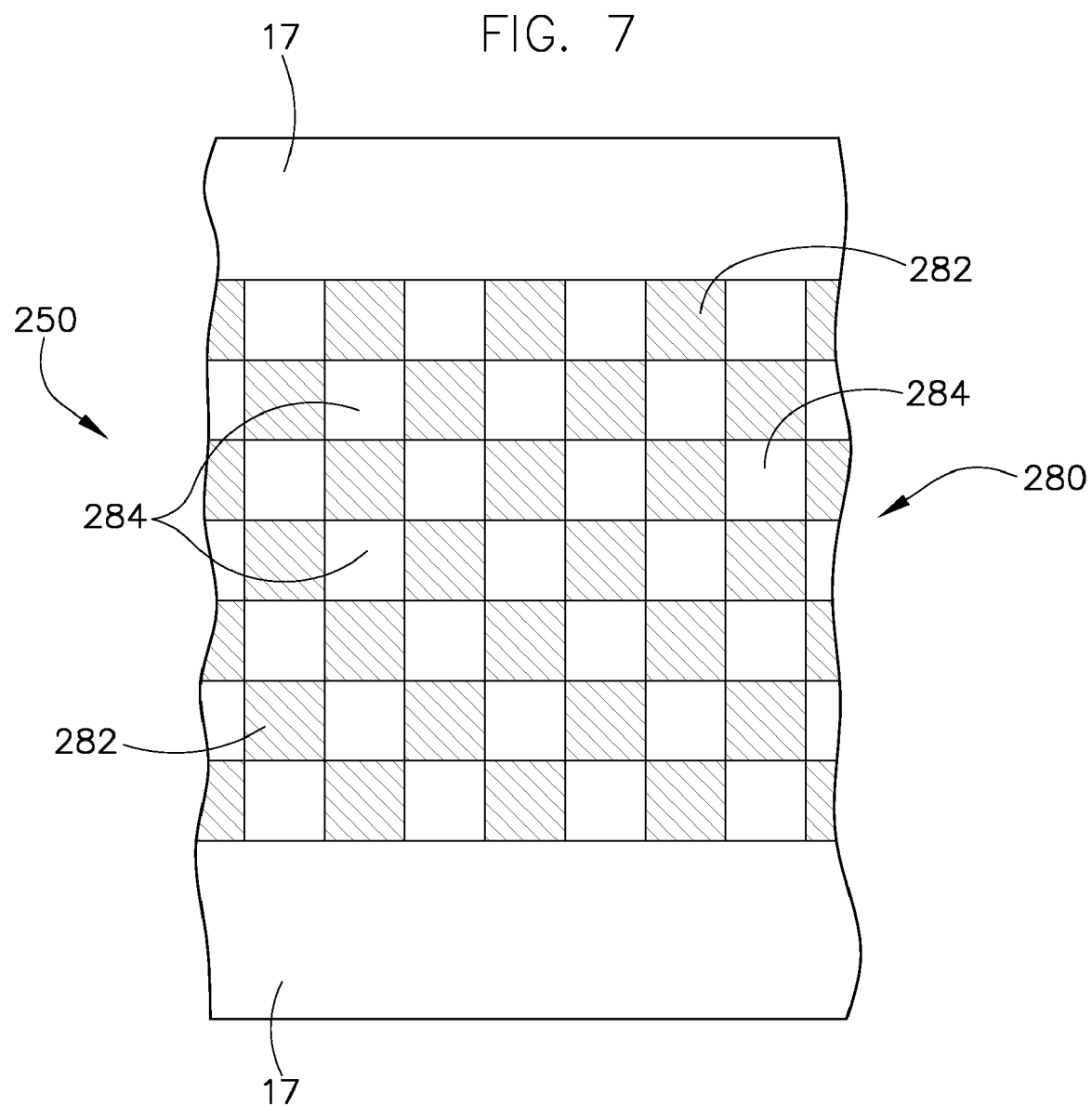
FIG. 7 is a plan view of a checkerboard filter according to embodiments of the invention.

FIG. 7 shows a checkerboard filter 250 for use with x-ray source 14 such as that described above with respect to embodiments of FIGS. 5 and 6. Checkerboard filter 250 includes a checkerboard pattern 280 and is positioned between the rails 17, shown in FIG. 3, such that the checkerboard pattern 280 is substantially arranged over the pixels 50 as illustrated in the detector 20 of FIG. 4, and having a one-to-one correspondence therewith. In this embodiment, pattern 280 includes an alternating arrangement of elements filled with filter material 282 having x-ray attenuating properties, and elements comprising openings 284. Each element 282, 284 within the checkerboard pattern 280 corresponds to a pixel 50 of detector 20. Thus, x-rays impinging upon pixels 50 that pass through the filter materials 282 will be attenuated thereby, and x-rays impinging upon pixels 50 that pass through the openings 284 will not be attenuated thereby as they pass therethrough. In alternate embodiments, the openings can contain materials that shape the x-ray spectrum in a desired manner.

Figure 8:
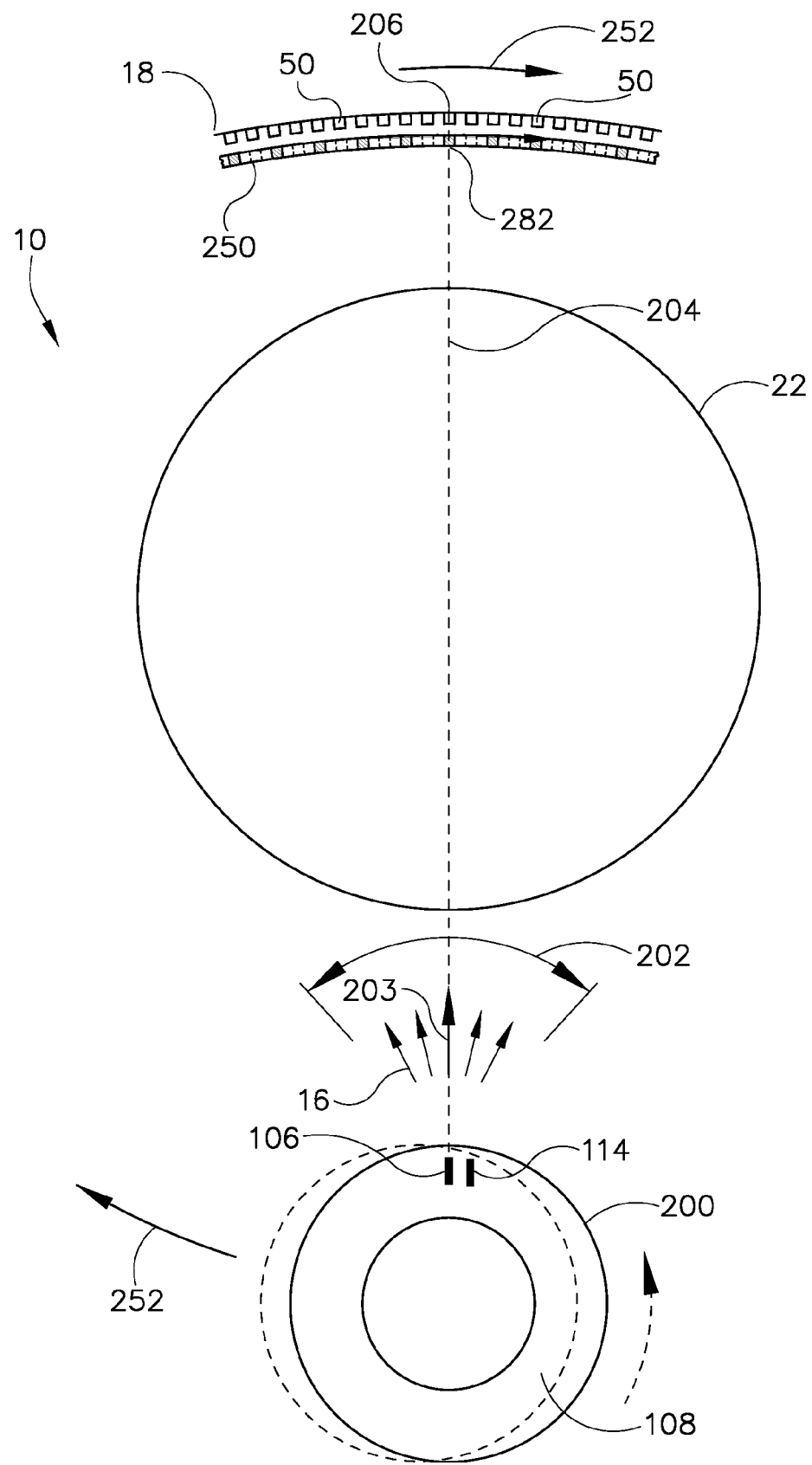
FIGS. 8-9 are schematic illustrations of a single slice of a cross-sectional view of a CT imaging system according to embodiments of the invention.
Figure 9:
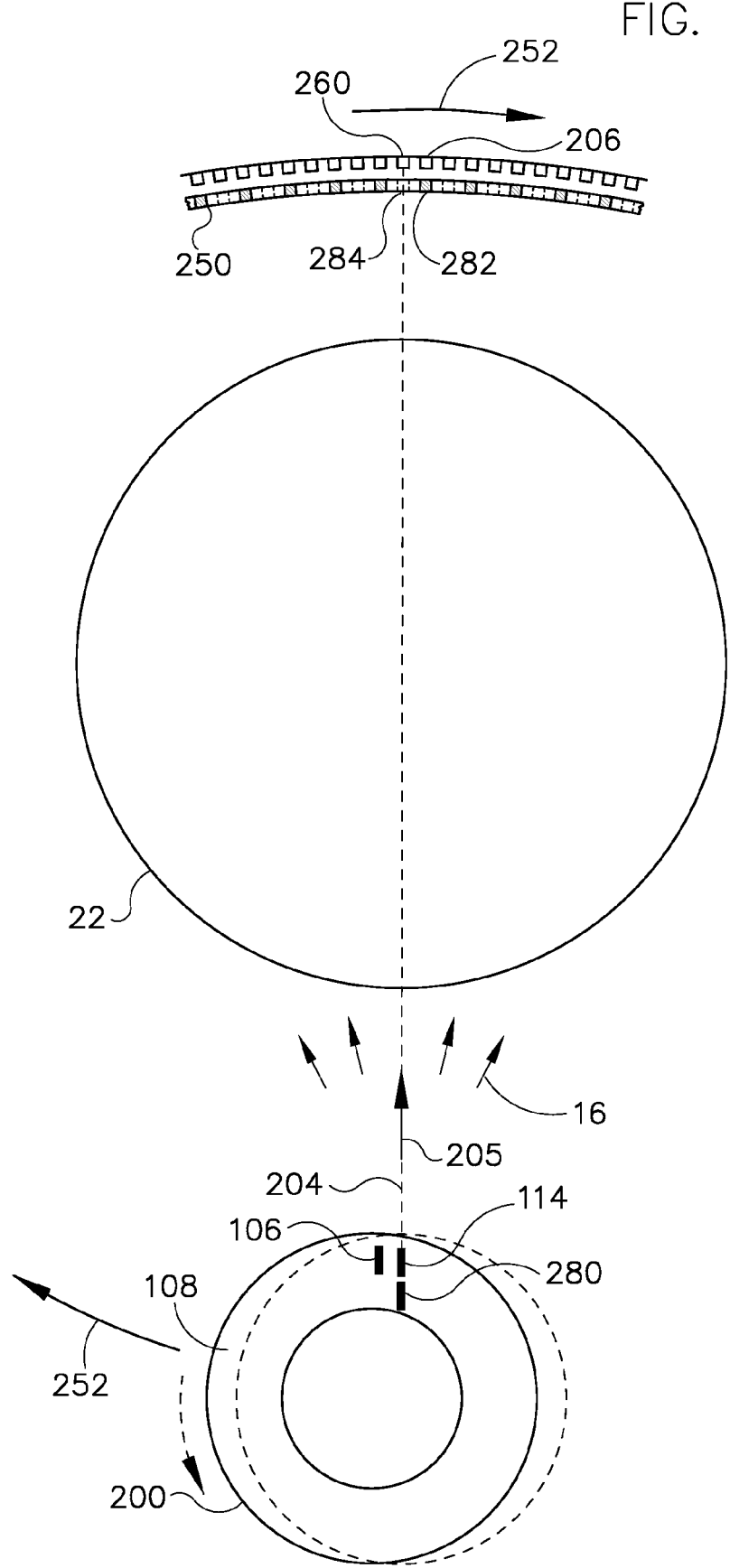

FIGS. 8 and 9 show schematic illustrations of a single slice of a cross-sectional view of a CT imaging system 10 for two adjacent rotational positions of a gantry (not shown) such as gantry 12 according to an embodiment of the invention. In one embodiment, subject 22 is not translated through the gantry bore (not shown) such that an axial scan may be performed. FIG. 8 illustrates emission of x-rays 16 from the first focal spot position 106, and FIG. 9 illustrates emission of x-rays 16 from the second focal spot position 114. CT imaging system 10 includes a detector assembly 18 having pixels 50 therein. To simplify illustration, pixels 50 are illustrated as being positioned directly within the detector assembly 18. However, one skilled in the art would recognize that the pixels 50 may be positioned within detector modules 20, as described above in relation to FIGS. 1-4, and the detector modules 20 may be positioned within a detector assembly 18.

Pixels 50 are positioned to receive x-rays 16 that pass through an object 22. X-rays 16 emit from anode 200 and of x-ray source 14 as illustrated and described above with respect to FIGS. 5 and 6. As described above, the anode 200 includes a first focal spot 106 and a second focal spot 114. According to one embodiment of the invention, the anode 200 is caused to rotate at a high speed of rotation such as, for instance, 130 Hz. Focal spots 106, 114 are electrode focal spots for filaments 102 or 120, 122 and remain stationary relative to filaments 102 or 120, 122. Accordingly, while the anode 200 may be caused to rotate at a high speed of rotation, filament focal spots 106, 114 do not rotate with respect to anode 200. It is contemplated, however, that the anode 200 may be stationary according to another embodiment of the invention. The detector assembly 18 and the anode 200 are coupled to the gantry while the gantry is caused to rotate 252 about the object 22 to be imaged.

As shown in FIG. 8, x-rays 16 emit in a fan angle 202 from the first focal spot position 106. A central ray 203 of x-rays passes from the first focal spot 106, along ray 204 through the object 22, and impinges upon a first pixel 206 within detector assembly 18. Prior to impinging upon first pixel 206, central ray 203 passes through a filter material 282 of checkerboard filter 250. Other x-rays 16 impinge upon respective pixels 50 of detector assembly 18, also after passing through respective elements 282 or 284 of checkerboard filter 250 as illustrated in FIG. 7. Data acquired from pixels 50 thus represent data acquired from x-rays 16 having passed through respective subject trajectories, one such trajectory being ray 204, and having passed through respective elements 282 or 284 of checkerboard filter 250.

FIG. 9 shows that the gantry has rotated a short distance along the rotation direction 252, as compared to its position in FIG. 8. In particular, the gantry has rotated to a position such that the position of second focal spot 114 intersects ray 204. Because of the change in position of the gantry from that shown in FIG. 8, the x-rays 16 that emit from the second focal spot 114 include a central ray 205 that passes along the trajectory 204 within the object 22, which is the same trajectory 204 that central ray 203 passed along as shown in FIG. 8. Accordingly, central rays 203, 205 each traverse the object 22 along the same trajectory 204. Similarly, other x-rays 16 of FIG. 9 impinge upon respective pixels 50 of detector assembly 18 also after passing through subject trajectories that x-rays 16 of FIG. 8 also passed through. According to an embodiment of the invention, an x-ray 16 of FIG. 9 that passes through a same subject trajectory as another x-ray 16 of FIG. 8 passes through an element 282, 284 of checkerboard 250 neighboring the element 282, 284 through which the x-ray 16 of FIG. 8 passed. For example, while central ray 203 passes along ray 204 and through filter material 282 to impinge upon first pixel 206, central ray 205 passes along ray 204 and through an opening 284 of the checkerboard filter 250 before impinging on a second pixel 260. In one embodiment, opening 284 and a second pixel 260 are each neighbors of filter material 282 and first pixel 206, respectively.

One skilled in the art will recognize that the spacing, or offset 118 between focal spots 106, 114 (as illustrated in FIGS. 5 and 6), the timing of focal spot emission, the rate of view sampling, the detector cell size, and the rotation rate of the gantry, can be appropriately selected such that x-ray emission from the first focal spot 106 and subsequently from the second focal spot 114 emit x-rays along substantially similar trajectories such as trajectory 204. Thus, two sets of energy sensitive projection data may be acquired having source positions that are geometrically aligned with respect to the object 22. Both sets of projection data are acquired which pass along the trajectory 204, but emit from separate focal spots 106, 114. Because an emission from the first focal spot 106 passes along trajectory 204 and through the filter material 282, and because another emission from the second focal spot 114 passes along trajectory 204 and through an opening 284, the two sets of data are aligned with the object 22 while having differing levels of attenuation and hence different spectra, despite having substantially the same x-ray source energy at the two focal spots 106, 114.

In the embodiments illustrated in FIGS. 8 and 9, the two focal spots 106, 114 are offset 118 from one another in XY by an amount dictated by the geometry and operation of the imaging system 10. In one embodiment the first and second focal spot positions are offset in XY a distance of $2*\pi*R_{FS}/(N)$, where $R_{FS}$ is the radius from the focal spot to iso-center, and N is a number of views of acquired data. The detector resolution and number of views is selected such that, during the scanning interval for one view, the detector is rotated so that an adjacent detector cell next occupies the location of the previous detector cell. In alternate embodiments, the resolution and number of views can be selected such that the detector rotates by an odd number of detector cells from one view position to the next. Furthermore, an offset 118 in only the XY plane will accommodate an axial scanning sequence.

According to another embodiment of the invention, and referring again to FIGS. 8 and 9, two sets of energy discriminatory projection data may be acquired without the presence of the checkerboard filter 250. Instead of passing x-rays along trajectory 204 and through filter material 282 from the first focal spot 106, and passing x-rays along trajectory 204 and through opening 284 from the second focal spot 114, energy discrimination data is acquired by employing fast kVp switching. In this embodiment, the x-ray controller, such as the x-ray controller 28 of FIG. 2, causes x-rays 16 to emit from the first focal spot 106 at a first kVp, and the x-ray controller 28 causes x-rays 16 to emit from the second focal spot position 114 at a second kVp.

In this embodiment, x-rays 16 emit from the first focal spot 106 along the trajectory, or ray 204, pass through the object 22, and impinge on the first pixel 206 positioned in the detector assembly 18. As the gantry continues to rotate along path 252, x-rays 16 are next caused to emit from the second focal spot 114 and, because of the gantry rotation, the x-rays impinge on the second pixel 260 after passing along the path 204 within the object 22. Thus, two sets of energy discriminating projection data may be acquired having source positions that are geometrically aligned with respect to the object 22. However, in this embodiment, the energy discriminating data is acquired with the use of fast kVp switching instead of by the use of a checkerboard filter. As an example, the x-rays 16 emit at a first kVp, such as for instance 80 kVp, when emitting from the first focal spot 106 to the first pixel 206, and emit at a second kVp, such as for instance 140 kVp, when emitting from the second focal spot 112 to the second pixel 260. As such, spatially overlapping sets of energy sensitive data may be obtained to enable material decomposition or effective Z estimation.

One skilled in the art will recognize that the two embodiments described herein may be combined to improve and enhance the effect of both. In other words, a checkerboard filter may be used in conjunction with fast kVp switching to further enhance the energy discriminating data that may be acquired.

One skilled in the art will also recognize that the embodiments described herein are not limited to axial scanning. For instance, during a helical scan, energy sensitive data may be acquired from both focal spots 106, 114 by offseting the focal spots in both the XY direction as described above, and additionally by emitting the second focal spot from a position that is also offset in the Z direction.

Referring again to FIG. 9, instead of emitting electrons toward the second focal spot 114, during a helical scan, the offset in Z that occurs can be compensated for by offsetting the focal spot position in Z as well to an alternate second focal spot 280. Because the focal spots 106, 114, 280 are positioned on a beveled surface 108 of the anode 200, one skilled in the art would recognize that the second focal spot 280 may be offset in Z by offseting the focal spot position 280 in a radial direction from position 114 on the anode. In another embodiment where x-ray source 14 comprises a stationary anode 200, the second focal spot can be offset in both XY and Z.

Accordingly, referring back to FIGS. 8 and 9, in operation during a helical scan, x-rays 16 emit from the first focal spot position 106 along the trajectory, or ray 204, pass through the object 22, and impinge on the first pixel 206 positioned in the detector assembly 18. However, as the gantry 12 continues to rotate along path 252, because the object 22 continuously translates through the gantry bore in a helical scan, the trajectory 252 through the object 22 is offset in Z as well. Accordingly, x-rays 16 are caused by the controller 28 to emit from the alternate second focal spot 280 that is offset in both the XY plane and in Z as well (as opposed to the second focal spot position 114 being offset in only XY in the axial scan). Because of both the gantry rotation 252 and the object 22 translation, the x-rays impinge on a pixel that is neighboring the second pixel 260, and impinge thereon after passing along the path 204 within the object 22. One skilled in the art will recognize that two sets of energy sensitive data may be acquired for a helical scan using either a checkerboard filter 250 or by fast kVp switching, as described above.

The two focal spots 106, 280 are offset in Z by an amount equal to $P_h * D/(M_g * N)$, wherein $P_h$ is a helical pitch, D is a size of the detector, $M_g$ is a magnification factor of the gantry, and N is a number of views of acquired data. In alternate embodiments, the resolution and number of views and offset in Z can be selected such that the detector rotates by an odd number of detector cells from one view position to the next. The offset in Z is in addition to the offset 118 as described with respect to the axial scan. One skilled in the art would recognize that, referring to FIG. 5, electrodes (not shown) may be placed on the cathode fore and aft of the filament 102 to effectuate a wobble in the Z direction. Likewise, one skilled in the art would recognize that, referring to FIG. 6, the filaments 120, 122 may be offset from one another fore and aft, to accommodate the offset in the Z position of the focal spot 280 with respect to the first focal spot 106. In one embodiment, the rotation speed of the gantry, number of views, detector resolution, and helical pitch may be such that the offset in Z can be neglected.

Figure 10:
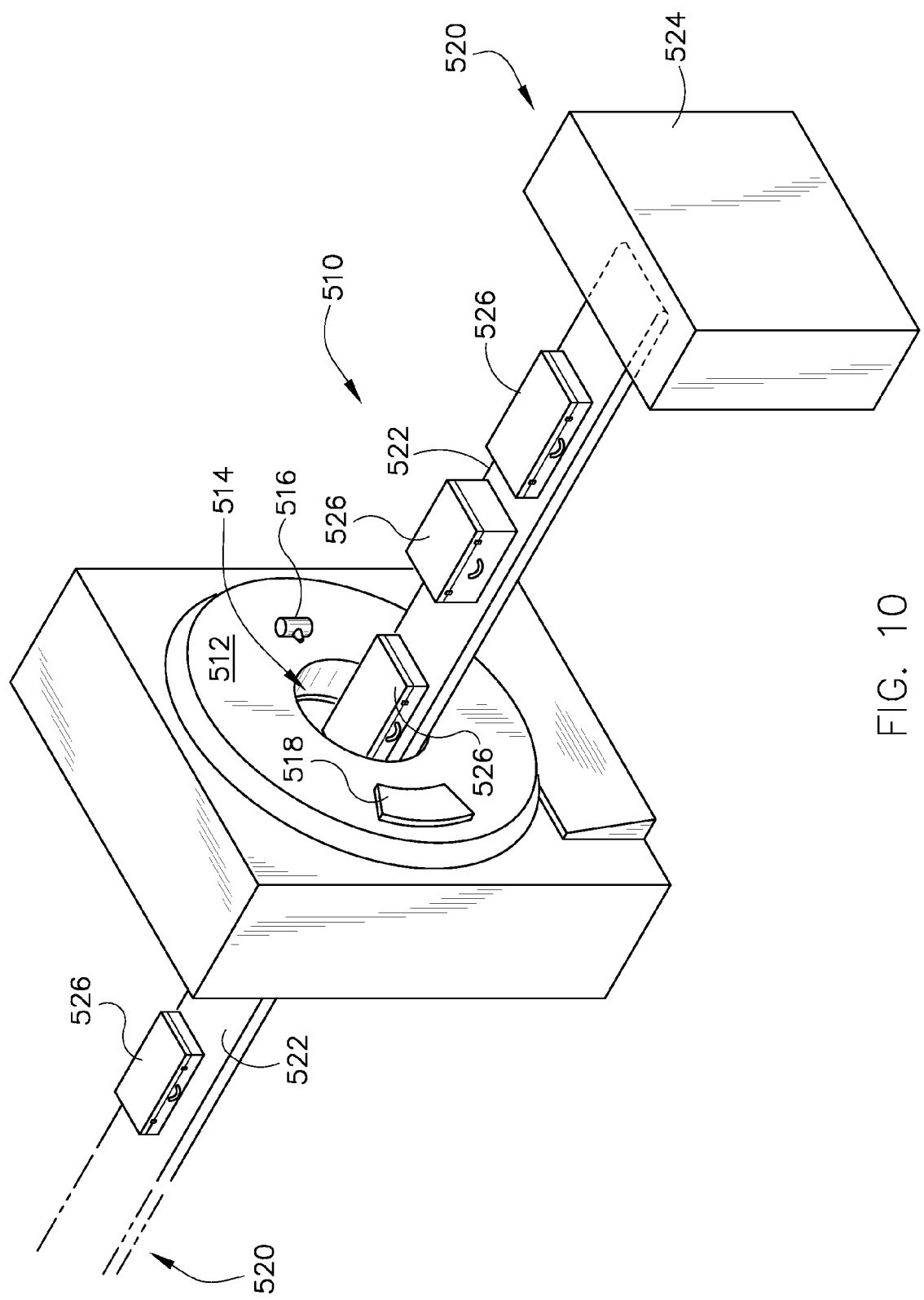
FIG. 10 is a pictorial view of a CT system for use with a non-invasive package inspection system according to an embodiment of the invention.

Referring now to FIG. 10, package/baggage inspection system 510 includes a rotatable gantry 512 having an opening 514 therein through which packages or pieces of baggage may pass. The rotatable gantry 512 houses a high frequency electromagnetic energy source 516 as well as a detector assembly 518 having scintillator arrays comprised of scintillator cells similar to that shown in FIG. 4. A conveyor system 520 also is provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc.

An implementation of the system 10 and/or 510 in an example comprises a plurality of components such as one or more of electronic components, hardware components, and/or computer software components. A number of such components can be combined or divided in an implementation of the system 10 and/or 510. An exemplary component of an implementation of the system 10 and/or 510 employs and/or comprises a set and/or series of computer instructions written in or implemented with any of a number of programming languages, as will be appreciated by those skilled in the art. An implementation of the system 10 and/or 510 in an example comprises any (e.g., horizontal, oblique, or vertical) orientation, with the description and figures herein illustrating an exemplary orientation of an implementation of the system 10 and/or 510, for explanatory purposes.

An implementation of the system 10 and/or the system 510 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 510 comprises the recordable data storage medium of the image reconstructor 34, and/or the mass storage device 38 of the computer 36. A computer-readable signal-bearing medium for an implementation of the system 10 and/or the system 510 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 510, for instance, one or more of a telephone network, a local area network ("LAN"), a wide area network ("WAN"), the Internet, and/or a wireless network.

A technical contribution for the disclosed method and apparatus is that it provides for a computer-implemented apparatus and method of acquiring imaging data at more than one energy range using a multi-energy imaging source modulated at multiple-view intervals.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Furthermore, while single energy and dual-energy techniques are discussed above, the invention encompasses approaches with more than two energies. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A CT system, comprising:
   a rotatable gantry having an opening for receiving an object to be scanned;
   at least one x-ray source coupled to the gantry and configured to project x-rays toward the object, the at least one x-ray source further comprising an anode comprising a first anode focal spot position and a second anode focal spot position;
   a detector coupled to the gantry and having a scintillator therein and configured to receive x-rays that pass through the object;
   a generator configured to energize the at least one x-ray source; and
   a controller configured to:
      energize the generator to project a first beam of x-rays toward the object from the first anode focal spot position of an anode, the first beam of x-rays having a ray traversing a first path through the object;
      acquire imaging data from the first beam of x-rays;
      position the at least one x-ray source such that a second beam of x-rays projected from the second anode focal spot position of the anode has a ray directed to traverse a second path through the object, the second anode focal spot position different than the first anode focal spot position, wherein the first path and second path through the object are the same; wherein the controller, in being configured to position the at least one x-ray source, is configured to position the second anode focal spot position of the at least one x-ray source such that the second beam of x-rays has a second Z-position different from a first Z-position of the first beam of x-rays;
      energize the generator to project the second beam of x-rays toward the object; and
      acquire imaging data from the second beam of x-rays.

2. The CT system of claim 1, wherein the at least one x-ray source comprises a cathode configured to:
   emit a beam of electrons toward the first anode focal spot position to generate the first beam of x-rays; and
   deflect the beam to the second anode focal spot position to generate the second beam of x-rays.

3. The CT system of claim 2, wherein the cathode is configured to deflect the beam using one of electromagnetic deflection and electrostatic deflection.

4. The CT system of claim 1, wherein the generator is energized to a first kVp when projecting the first beam of x-rays and energized to a second kVp, different from the first, when projecting the second beam of x-rays.

5. The CT system of claim 1, wherein the detector comprises a checkerboard filter positioned between the scintillator and the object, the checkerboard filter having a first area positioned to pass the ray traversing in the first beam of x-rays, and having a second area positioned to pass the ray traversing in the second beam of x-rays.

6. The CT system of claim 5, wherein the first area is a material selected to attenuate x-rays that pass therethrough, and wherein the second area comprises an opening through which x-rays pass unimpeded.

7. The CT system of claim 1, wherein the anode is one of a rotating and a stationary anode.

8. The CT system of claim 1, wherein the controller is configured to:
   translate the object in Z; and
   wherein the controller, in being configured to position the at least one x-ray source, is configured to position the second anode focal spot position of the at least one x-ray source such that the second beam of x-rays has a second Z-position different from a first Z-position of the first beam of x-rays.

9. The CT system of claim 8, wherein the first Z-position and the second Z-position are offset in Z by an amount equal to $Ph*D/(Mg*N)$; and
   wherein Ph is a helical pitch, D is a size of the detector, Mg is a magnification factor of the gantry, and N is a number of views of acquired data.

10. The CT system of claim 1, wherein the first and second focal spot positions are offset from one another on the anode in at least an XY direction of the CT system.

11. The CT system of claim 10, wherein the first and second focal spot positions are offset in XY a distance of:
   $2*n*RFS/(N)$;
   wherein RFS is the radius from the focal spot to iso-center, and N is a number of views of acquired data.

12. The CT system of claim 1, wherein the at least one x-ray source comprises two cathodes and wherein the generator is configured to energize one of the two cathodes to project the first beam of x-rays and to energize the other of the two cathodes to project the second beam of x-rays.

13. A method of acquiring energy sensitive CT imaging data in a CT imaging system, comprising:
   moving a first anode focal spot of an x-ray source to a first position with respect to an object to be scanned;
   projecting a first beam of x-ray energy toward an object from the first anode focal spot positioned in the first position;
   acquiring a first projection of imaging data from the first beam of x-ray energy;
   projecting a second beam of x-ray energy toward the object from a second anode focal spot positioned in the first position, the second anode focal spot being positioned at a different position on an anode than the first anode focal spot;
   acquiring a second projection of imaging data from the second beam of x-ray energy; and
   offsetting the first anode focal spot and the second anode focal spot from one another on the anode in at least an XY plane of the CT imaging system.

14. The method of claim 13, comprising positioning a checkerboard filter between the object and a pixelated scintillator positioned to receive x-rays that pass through the object.

15. The method of claim 13, wherein the first beam of x-ray energy is energized to at a first kVp when projecting the first beam of x-rays and energized to the second beam of x-ray energy is at a second kVp, different from the first, when projecting the second beam of x-rays wherein the second kVp is different than the first kVp.

16. The method of claim 13, projecting the first beam using a first filament and projecting the second beam using a second filament.

17. The method of claim 13, wherein, during a helical scan, further comprising moving the second anode focal spot in Z by an amount equal to:

$P_h *D/(M_g *N)$;

wherein $P_h$ is a helical pitch, D is a size of a detector, $M_g$ is a magnification factor of a gantry, and N is a number of views of acquired data.

18. The method of claim 13, comprising offsetting the first anode focal spot and offsetting the second anode focal spot from one another on the anode in at least an XY direction of a CT imaging system is at a distance of:

$2*n*RFS/(N)$;

wherein RFS is the radius from the focal spot to iso-center, and N is a number of views of acquired data.

19. The method of claim 13, comprising projecting the first and second beams using a single filament.

20. The method of claim 19, comprising projecting the second beam after electrostatically or electromagnetically deflecting a plurality of electrons.

* * * * *

UNITED STATES PATENT AND TRADEMARK OFFICE
CERTIFICATE OF CORRECTION

| | |
|---|---|
| PATENT NO. | : 7,852,979 B2 |
| APPLICATION NO. | : 11/954295 |
| DATED | : December 14, 2010 |
| INVENTOR(S) | : Edic et al. |

It is certified that error appears in the above-identified patent and that said Letters Patent is hereby corrected as shown below:

On the Face Page, in Field (56), under "OTHER PUBLICATIONS", in Column 2, Line 1, delete "Reconstruction" and insert -- Reconstructions --, therefor.

In Column 12, Line 24, in Claim 9, delete "Ph*D/(Mg*N);" and insert -- $P_h*D/(M_g*N)$; --, therefor.

In Column 12, Line 25, in Claim 9, delete "Ph" and insert -- $P_h$ --, therefor.

In Column 12, Line 25, in Claim 9, delete "Mg" and insert -- $M_g$ --, therefor.

In Column 12, Line 33, in Claim 11, delete "2*n*RFS/(N);" and insert -- $2*\pi*R_{FS}/(N)$; --, therefor.

In Column 12, Line 34, in Claim 11, delete "RFS" and insert -- $R_{FS}$ --, therefor.

In Column 14, Line 5, in Claim 18, delete "2*n*RFS/(N);" and insert -- $2*\pi*R_{FS}/(N)$; --, therefor.

In Column 14, Line 6, in Claim 18, delete "RFS" and insert -- $R_{FS}$ --, therefor.

Signed and Sealed this
Twenty-first Day of June, 2011

David J. Kappos
*Director of the United States Patent and Trademark Office*